United States Patent
Nacson

(10) Patent No.: US 9,213,123 B2
(45) Date of Patent: Dec. 15, 2015

(54) NON-INVASIVE METHOD AND APPARATUS FOR DETECTING THE PRESENCE OF ILLICIT SUBSTANCES

(76) Inventor: Sabatino Nacson, Thornhill (CA)

( * ) Notice: Subject to any disclaimer, the term of this patent is extended or adjusted under 35 U.S.C. 154(b) by 412 days.

(21) Appl. No.: 13/637,271

(22) PCT Filed: Mar. 25, 2011

(86) PCT No.: PCT/CA2011/000313
§ 371 (c)(1),
(2), (4) Date: Sep. 25, 2012

(87) PCT Pub. No.: WO2011/116473
PCT Pub. Date: Sep. 29, 2011

(65) Prior Publication Data
US 2013/0019654 A1    Jan. 24, 2013

Related U.S. Application Data

(60) Provisional application No. 61/317,944, filed on Mar. 26, 2010.

(51) Int. Cl.
*G01V 11/00* (2006.01)
*G01V 5/00* (2006.01)
(Continued)

(52) U.S. Cl.
CPC ...... *G01V 11/00* (2013.01); *G01N 1/24* (2013.01); *G01V 5/0008* (2013.01); *G01N 2001/024* (2013.01)

(58) Field of Classification Search
CPC .............. G01N 2001/022; G01N 2001/024; G01N 1/24; G01N 33/0009; G01N 33/0031; G01N 2201/0221; G01N 2001/027; G01V 5/0008; G01V 11/00

USPC .......... 73/23.2, 863.81, 863.83, 864, 864.73, 73/863, 28.01, 31.05, 23.33, 23.41, 31.01, 73/31.02, 31.03, 863.41

See application file for complete search history.

(56) References Cited

U.S. PATENT DOCUMENTS

| 5,395,589 A | 3/1995 | Nacson |
| 5,859,375 A | 1/1999 | Danylewych-May et al. |
| 6,026,135 A * | 2/2000 | McFee et al. ................. 376/159 |

(Continued)

FOREIGN PATENT DOCUMENTS

CA    2129594 A1    2/1996

*Primary Examiner* — Daniel S Larkin
*Assistant Examiner* — Jamar Ray
(74) *Attorney, Agent, or Firm* — Kagan Binder, PLLC

(57) ABSTRACT

The present invention is directed to a system for screening the content of the air proximate to a target for the presence of one or more illicit substances by using a chemical detector, a metal detector and a radiation detector all houses within a portable detection unit that may be carried by hand to detect threat substances on a target. The system also comprises a support module that is coupled either wirelessly or though a conduit to the portable detection unit to support the operations of the portable detection unit by proving processing and analysis of the detected results and power. The system also comprises a vacuum source for drawing air proximate to the target into the portable detection unit for vaporization and analysis. The vacuum source may be within the support module and drawing air through a hose in the conduit, or may be within the portable detection unit itself. The system may be used by passing the portable detection unit over or near to a target in a manner similar to airport metal detectors.

11 Claims, 2 Drawing Sheets

(51) Int. Cl.
*G01N 1/24* (2006.01)
*G01N 1/02* (2006.01)

(56) References Cited

U.S. PATENT DOCUMENTS

| | | |
|---|---|---|
| 6,610,977 B2 | 8/2003 | Megerle |
| 6,690,005 B2 | 2/2004 | Jenkins et al. |
| 7,299,710 B2 | 11/2007 | Syage |
| 8,259,299 B2 * | 9/2012 | Harra et al. .................. 356/437 |
| 8,756,975 B2 * | 6/2014 | Wu .............................. 73/31.05 |
| 2002/0148305 A1 | 10/2002 | Danylewych-May et al. |
| 2005/0061056 A1 * | 3/2005 | Sunshine et al. ............... 73/23.2 |
| 2007/0056388 A1 * | 3/2007 | Henry et al. ................ 73/863.12 |
| 2007/0137319 A1 | 6/2007 | Nacson et al. |
| 2009/0295391 A1 * | 12/2009 | Bosnar ......................... 324/329 |
| 2014/0219315 A1 * | 8/2014 | Adams et al. ................ 374/164 |

\* cited by examiner

NON-INVASIVE METHOD AND APPARATUS FOR DETECTING THE PRESENCE OF ILLICIT SUBSTANCES

RELATED APPLICATION

This application claims the benefit from International Application No. PCT/CA2010/000313, which was filed on Mar. 25, 2011, which in turn claims priority under 35 U.S.C. §119(e) to U.S. Provisional Application No. 61/317,944, filed Mar. 26, 2010, both of which are incorporated herein by reference in their entireties.

FIELD OF THE INVENTION

The present invention relates generally to screening persons freight, luggage and other items, and in particular, to a non-invasive method and apparatus for detecting the presence of illicit substances on a target.

BACKGROUND OF THE INVENTION

It is common practice to screen targets, including people, freight, luggage and other items, to detect the presence of illicit substances. Illicit substances include, for example, weapons, narcotics, explosives, chemical warfare agents, biological warfare agents, nuclear or radiological agents, ammunitions, toxic industrial chemicals or waste, and controlled or contraband items such as tobacco.

This screening is often conducted in locations where security or safety is a principal concern, such as at a border crossing between countries, or in an airport or another transportation hub. It may be done to guard against terrorism, prevent the movement of weapons or drugs, or to control trade.

Traces of illicit substances may be present on people who carry, handle or otherwise come into contact with illicit substances. For example, concealed explosives or other illicit substances under garments may emit vapors, which may be detected through clothes or other packaging. The processing of concealing the illicit substances may have left microscopic traces of the illicit substance on a person, or on the surfaces that have come into contact with the illicit substance. Detection of these substances requires costly and bulky equipment which may require specialized training to operate, which has discouraged their wide-spread use.

Illicit substances that contain radioactive particles may be detected using a variety of technologies, such as sodium iodide detectors, or technologies exploiting a Geiger-Mueller tube, each of which is a stand-alone device.

To detect these substances on a person or on luggage or other items, a person may be physically examined (i.e. patted down) for unusual items, and items may be swabbed and the samples analyzed for traces of illicit materials. Dogs are sometimes used to detect illicit materials, but must be specially trained to do so, at considerable time and expense. To detect weapons, metal detectors using magnetic fields are typically employed on people, and x-ray technologies on items that can tolerate the radiation.

These methods are time consuming and costly. It may take many minutes to perform these steps to a person and their luggage in a typical scenario, such as in an airport, using separate devices and separate personnel. A busy airport may move many thousands of individuals, and their luggage, a day through its gates, and performing all of these steps separately in such an airport would be an enormous and costly undertaking using current technologies. There is a need for a system that screens for all of these threatening target substances simultaneously.

SUMMARY OF THE INVENTION

The invention is directed to a system for screening a target for the presence of one or more target substances comprising:
 a portable detection unit having: a metal detection module for detecting metal proximate to the portable detection unit; a radiation detection module for detecting harmful radiation proximate to the portable detection unit; and at least one chemical detection module having an inlet and an outlet;
 a support module having a vacuum source and a power source;
 a conduit between the support module and the outlet which permits the movement of air from the portable detection unit to the vacuum source and the transmission of power from the power source to the portable detection unit to power its modules;
 wherein when the vacuum source is actuated and the portable detection unit is positioned near to the target, air is drawn from the surroundings proximate to the portable detection unit through the inlet into the chemical detection module for analysis and detection of target substances in the air near the target, and
 wherein a target substance is detected by the portable detection unit when metal detection module, the radiation detection module, or the one chemical detection detect the presence of a target substance.

The invention is also directed to a system for screening a target for the presence of one or more target substances comprising:
 a portable detection unit having: a metal detection module for detecting metal proximate to the portable detection unit; a radiation detection module for detecting harmful radiation proximate to the portable detection unit; at least one chemical detection module having an inlet; a wireless transceiver; a vacuum source for drawing air through the inlet and the at least one chemical detection module when actuated; and
 a power source for powering the portable detection unit; and
 a support module having a second wireless transceiver for wireless communication with portable detection unit through the wireless transceiver;
 wherein when the vacuum source is actuated and the portable detection unit is positioned near to the target, air is drawn from the surroundings proximate to the portable detection unit through the inlet into the chemical detection module for analysis and detection of target substances in the air near the target, and
 wherein a target substance is detected by the portable detection unit when metal detection module, the radiation detection module, or the one chemical detection detect the presence of a target substance.

The invention is also directed to a method of simultaneously screening a target for target substances using a device having a metal detection module for detecting metal target substances, and at least one chemical detection module for detecting the presence of target substances in the air surrounding a target. The method may also include a step of simultaneously checking for radiation near the target using the device which also comprises a radiation detection module.

Airborne particles and vapors of target substances emitted from a target are collected by the portable detection unit, which may contain a heated perforation through which the particles and vapors are drawn, vaporized and analyzed by a chemical detection module in the portable detection unit. The vaporized materials travel by the help of a miniature vacuum pump or other vacuum source into the ionization source of a compact, miniature ion mobility spectrometer, or other miniature chemical sensor technologies. The chemical sensor allows the detection of many volatile and non-volatile target substances in this manner.

The method and system also comprises a metal detection module, to detect all ferrous metallic objects with unrestricted scanning angles. Illicit substances that contain certain metals may induce a change in magnetic fields in range, which can be exploited to detect them. Non-ferrous metals may be detected by using the chemical sensor instead of the metal detection module.

The method and system may also comprise a radiation detection module having at least one radiation sensor for sensing radioactive particles, such as alpha, beta and gamma particles. Illicit substances that contain radioactive particles may be detected using a variety of technologies, such as sodium iodide detectors, or technologies exploiting a Geiger-Mueller tube, halogen-quenched Geiger-Mueller tube or similar technologies.

BRIEF DESCRIPTION OF THE DRAWINGS

Embodiments will now be described more fully with reference to the accompanying drawings in which.

DETAILED DESCRIPTION OF THE EMBODIMENTS

In the following, a method and system of combined explosives, metal and radiation monitoring technologies is described, for screening targets and the like by sampling the air within the targets to remove vapors and airborne particles from inside the targets and entrapping such vapors and airborne particles on a treated card for subsequent analysis.

Figure 1:
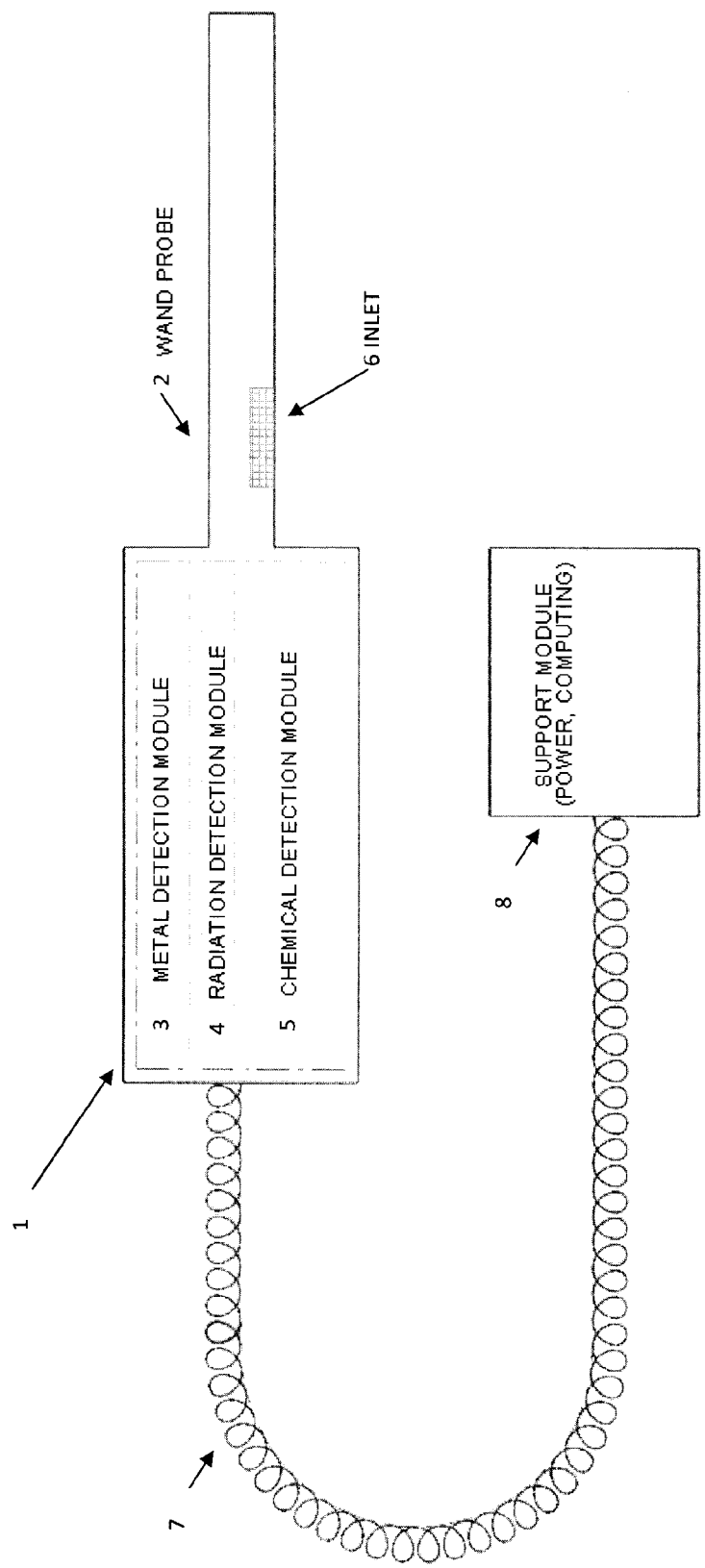
FIG. 1 shows a schematic of an embodiment of the invention having a detection wand and associated control system coupled by a conduit.

Turning now to FIG. 1, the screening system is shown to comprise a portable detection unit 1 coupled by a conduit 7 to a support module 8.

The portable detection unit 1 comprises a metal detection module 3 which detects the presence of metal proximate to the wand probe 2, a radiation detection module 4 for detecting the presence of radioactive particles proximate to the portable detection unit 1, and a chemical detection module 5 for detecting at least one illicit substance.

The metal detection module 3 uses a metal detector which detects changes in a magnetic field caused by the movement of ferrous objects through the field. One embodiment of such a metal detector would use an electromagnetic coil for inducing a magnetic field, and a sensor for detecting changes in the properties of the field or the current in the coil to infer the presence of a ferrous metal nearby. The electromagnetic coil may be housed within a wand probe 2 extending from the portable detection unit 1.

The portable detection unit 1 also comprises a radiation detection module 4 having at least one radiation sensor for sensing radioactive particles, such as alpha, beta and gamma particles. The radiation sensor may use a variety of technologies, such as sodium iodide detectors, or technologies exploiting a Geiger-Mueller tube, halogen-quenched Geiger-Mueller tube, or similar technologies, depending on the desired application.

The portable detection unit 1 also comprises at least one chemical detection module 5 for analyzing the chemical content of vapors, fluid droplets and particulates that are proximate to the portable detection unit 1. The chemical detection module may use any known chemical analysis technology, including, for example, miniature gas chromatographic analyzer, miniature mass spectrometer (stationary or portable), chemiluminescence detector, an axial ion mobility spectrometer (IMS), a field assymetric ion mobility spectrometry (FAIMS), a differential mobility spectrometer (DMS) or electrochemical sensors.

The chemical detection module 5 has an inlet 6 and an outlet fluidly connected the exterior of the portable detection unit 1. In a preferred embodiment, the inlet 6 comprises at least one perforation in the exterior housing of the wand probe 2, but the inlet 6 may be any opening to the exterior of the portable detection unit 1. Preferably, the inlet 6 is covered by a perforated surface or screen to prevent large particles from entering the chemical detection module 5 from the exterior of the portable detection unit 1.

The chemical detection module 5 also comprises a heating element which rapidly heats any vapors, fluid droplets and particulates when drawn into the inlet 6 to substantially vaporize them. The chemical content of the resulting vapor is analyzed by chemical detection module 5. In one embodiment, the heating element is integrated into the inlet 6, and comprises a heated screen.

The vapors, fluid droplets and particulates are drawn into the inlet 6 using a vacuum source. In this embodiment, the vacuum source is located in the support module 8, and the conduit 7 includes a hose coupled at one end to the vacuum source and the other end to the outlet of the portable detection unit 1. In operation, the vacuum source draws air bearing vapors, fluid droplets and particulates from the immediate surroundings into the inlet 6, through the heating element and into the at least one chemical detection module 5 for chemical analysis, and then through the outlet to be vented downstream of the vacuum source through a vent.

Residues from explosive materials are abundant on surfaces after handling explosive materials, and are difficult to remove. Volatile explosives, such as TATP, HMTD, EGDN, DMNB, NG, DNT and TNT are readily detected due to the fact that these explosives evaporate into the surrounding air even when concealed. Direct sampling of air proximate to a target provides a very reliable method of detecting illicit substances may be concealed in or on the target. The same applies to non-volatile explosives present as trace residue or particles adhering to clothes or surfaces such as pentaerythritol tetranitrate (PETN), cyclotrimethylenetrinitramine (RDX), octogen (HMX), 2,4,6,8,10,12-hexanitro-2,4,6,8,10, 12-hexaazaisowurtzitane (HNIW), octanitrocubane, and others.

The support module 8 also comprises a power supply which provides power to the modules in the portable detection unit 1 through a cable or cables in the conduit 7, and also provides a processor with memory for executing code for analyzing the results from the modules in the portable detection unit 7. The modules may communicate wirelessly with the support module 8, or though wires in the conduit 7.

Either the portable detection unit, the support module or both may have controls for controlling the operation of the screening system.

The portable detection unit may have at least one indicator, such as a LED light, to indicate when an illicit substance is detected. The indicator may also indicate which detection module or modules detected the illicit substance or substances. Either the portable detection unit, the support module, or both may have a display that displays to a user information regarding what the portable detection unit is currently detecting or has detected, including for example which sensor modules have detected an illicit substance, what illicit substance or substances have been detected, the concentration or composition of the illicit substances when applicable, and the date and time of the detection event for logging and evidentiary purposes.

During operation, when it is desired to screen a target for illicit substances, the portable detection unit 1 may be held close to the target, or moved about the target's surface. The portable detection unit 1 once turned on draws or vacuums air proximate to the target. The air proximate the target enters the chemical detection module 5 via the inlet 6. Air entering the chemical detection module 5 passes across the heating element of the before passing through the chemical detection module 5 and out the outlet to be drawn from the portable detection unit 1 through the conduit 7 by the vacuum source.

As the air is drawn through the portable detection unit 1, the air is heated by passing through a heating element to evaporate vapors, fluid droplets and particulates borne within the air. The chemical content of the vaporized matter in the air is analyzed automatically by chemical detection module 5 to detect the presence of illicit substances.

While the chemical detection module 5 is performing its detection and analysis, the user may continue to screen the target for metal or radioactive particles by moving or sweeping the portable detection unit 1 over the exterior surface of the target. The metal detection module 3 may detect metal at any number of locations proximate to the exterior surface of the target, and so the user may continue to scan and identify potential locations of metal on or within the target during the chemical analysis. Similarly, the user may continue to scan and identify locations of stronger radioactivity by moving the portable detection unit 1 over the exterior surface of the target, as the radiation detection module 4 may be used to localize a radiation source.

Upon completion of the chemical analysis, the target may be detained, confiscated or tagged if a positive indication of the presence of an illicit substance is encountered. Tagged targets that are tolerant of microwaves or x-rays may also be subjected to further screening using imaging technologies that exploit these kinds of radiation.

Although particular examples of analyzers are described above, those of skill in the art will appreciate that other suitable analyzers may be used. Those of skill in the art will also appreciate that some analytical techniques will be more efficient or preferred than others by virtue of various operational features, such as size, field deployment, need for inert carrier gases and susceptibility to potential chemical interferences that would normally be encountered in sampling complex chemical matrices found usually found in a particular sampling environments, such as a security checkpoint in an airport.

Figure 2:
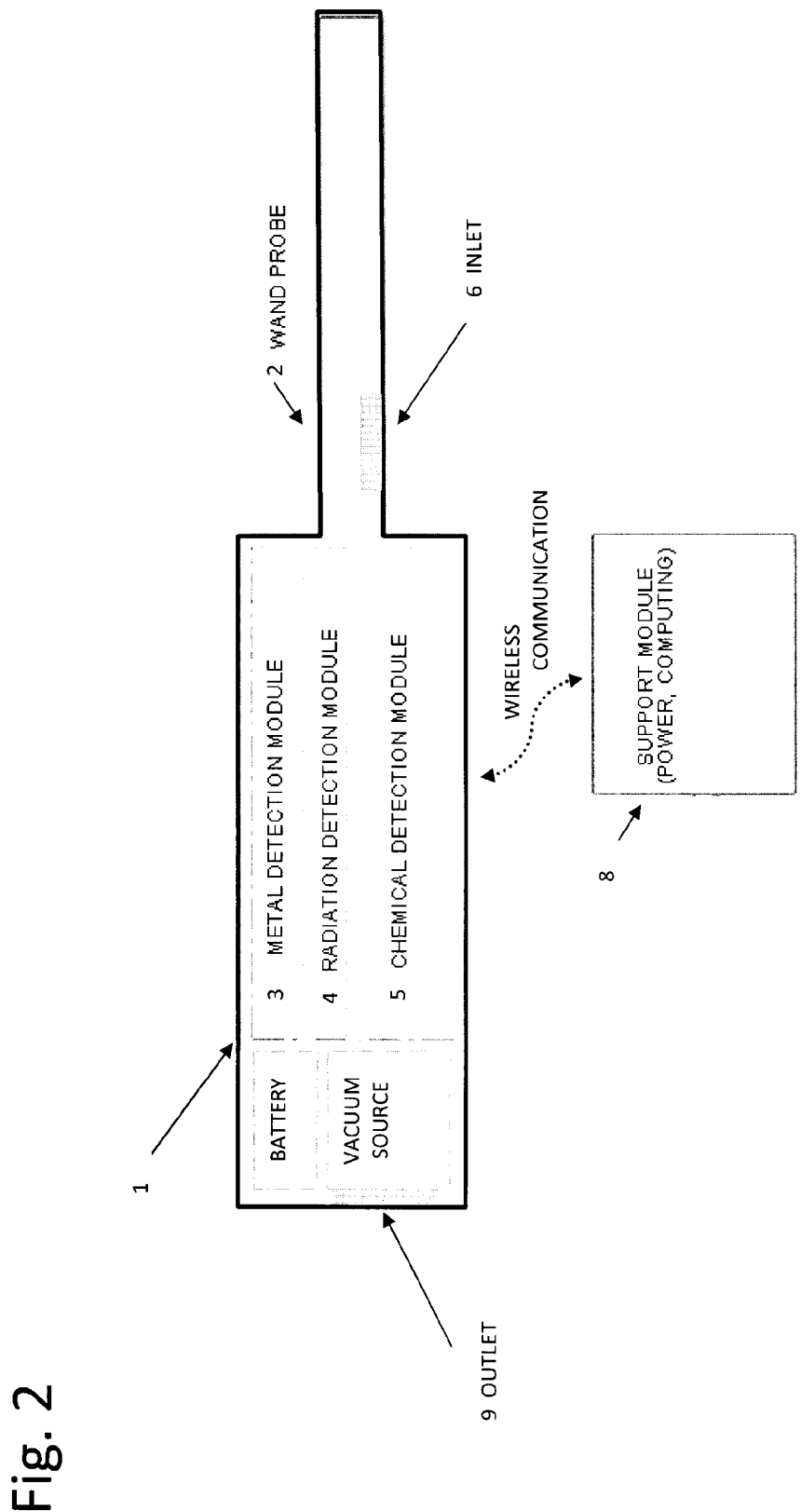
FIG. 2 shows a schematic of an embodiment of the invention having a detection wand and associated control system connected wirelessly.

In an alternative embodiment shown in FIG. 2, the portable detection unit 1 communicates wirelessly with the support module 8 instead of through a wired connection in the conduit. Both the portable detection unit 1 and the support module 8 have wireless transceivers to permit wireless communication between them using known methods. In this particular embodiment, the portable detection unit 1 is powered by a battery located within the portable detection unit 1, although the portable detection unit 1 could be powered by a conventional electrical cable plugged into an electrical outlet (which would be especially suitable if the transformers were located adjacent to the outlet and not positioned in the portable detection unit 1). The battery may be rechargeable, so that the portable detection unit 1 may be recharged when not in use.

The vacuum source is located in the portable detection unit 1 and is coupled directly to the chemical detection module 5, instead of being located in the support module. To reduce weight and power consumption, raw or crudely filtered results may be transmitted directed to the support module 8 for further processing, reducing the need for processors and memory within the portable detection unit. The remaining identified features of FIG. 2 perform the same functions as set out with respect to FIG. 1, but are adapted to fit the weight, space and power requirements of a wireless device.

In an alternative embodiment, multiple portable detection units are wirelessly linked to a single support module. The support module performs all of the processing for each of the detection units. This would allow a user of the system to use a portable detection unit while others are charging, or allow multiple users to use the portable detection units in a larger environment where there are multiple targets to be scanned at once.

In a preferred embodiment, the mass of the portable detection unit is distributed such that the portable detection unit is balanced about its handle, to reduce stress on the user.

Although embodiments have been described above with reference to the drawings, those of skill in the art will appreciate that variations and modifications may be made without departing from the invention as defined by the appended claims.

What is claimed is:

1. A system for screening a target for the presence of one or more target substances comprising:
   a. a portable detection unit having:
      i. a handle for use by a user to hold the unit and scan the target;
      ii. a metal detection module for detecting metal proximate to the portable detection unit; and
      iii. at least one chemical detection module having an inlet and an outlet;
   b. a support module having a vacuum source and a power source; and
   c. a conduit between the support module and the outlet which permits the movement of air from the portable detection unit to the vacuum source and the transmission of power from the power source to the portable detection unit to power the at least one chemical detection module,
   wherein, when the vacuum source is actuated and the portable detection unit is positioned proximate to the target, a sample of air is drawn from the air proximate to the portable detection unit through the inlet into the chemical detection module for analysis and detection of target substances in the sample of air, and
   wherein a target substance is detected by the portable detection unit when the metal detection module or the at least one chemical detection module detect the presence of the target substance in the sample of air.

2. The system of claim 1 further comprising a radiation detection module having at least one radiation sensor for sensing radioactive particles for detecting harmful radiation proximate to the portable detection unit, wherein the target substance is detected by the portable detection unit when the metal detection module, the radiation detection module, or the at least one chemical detection module detect the presence of the target substance in the sample of air.

3. The system of claim 2 further comprising a wand probe having an exterior housing, wherein the metal detection module comprises an electromagnetic coil housed within the wand probe, and the inlet comprises at least one perforation in the exterior housing of the wand probe.

4. The system of claim 1 further comprising a wand probe having an exterior housing, wherein the metal detection module comprises an electromagnetic coil housed within the wand probe, and the inlet comprises at least one perforation in the exterior housing of the wand probe.

5. The system of claim 1, wherein the system further comprises a heating element integrated into the inlet for heating the sample of air.

6. The system of claim 1, wherein the at least one chemical detection module comprises a sensor selected from the following group: a miniature gas chromatographic analyzer, a miniature mass spectrometer, a chemiluminescence detector, an axial ion mobility spectrometer, a field asymmetric ion mobility spectrometer, a differential mobility spectrometer, and an electrochemical sensor.

7. The system of claim 1, wherein the metal detection module detects a ferrous metal object by detecting a change induced in a magnetic field generated by the metal detection module when the metal detection module moves relative to the ferrous metal object.

8. The system of claim 1, wherein the chemical detection module detects non-ferrous metals by identifying the presence of non-ferrous metallic particles in the sample of air.

9. A method of screening a target for target substances using the system of claim 1, the target having an exterior surface, the method comprising placing the portable detection unit proximate to the exterior surface of the target, and moving the portable detection unit relative to the target around at least part of the exterior surface of the target while the vacuum source and detection modules are powered, wherein at least two detection modules are used simultaneously to detect target substances in the sample of air.

10. The method of claim 9 wherein the detection of target substances is indicated by an indicator or displayed on a display on the device.

11. The method of claim 9 wherein information indicating the detection of target substances is transmitted to a digital storage medium.

* * * * *